(12) United States Patent
Delphini

(10) Patent No.: US 11,596,802 B2
(45) Date of Patent: Mar. 7, 2023

(54) BIOFIELD APPARATUS

(71) Applicant: STARLIGHT INVESTMENTS, LLC, Emery, SD (US)

(72) Inventor: Sundara Delphini, Chico, CA (US)

(73) Assignee: Starlight Investments, LLC, Emery, SD (US)

(*) Notice: Subject to any disclaimer, the term of this patent is extended or adjusted under 35 U.S.C. 154(b) by 0 days.

(21) Appl. No.: 17/395,392

(22) Filed: Aug. 5, 2021

(65) Prior Publication Data

US 2022/0047881 A1 Feb. 17, 2022

Related U.S. Application Data

(60) Provisional application No. 63/064,712, filed on Aug. 12, 2020.

(51) Int. Cl.
*A61N 2/00* (2006.01)
*A61N 5/06* (2006.01)
(Continued)

(52) U.S. Cl.
CPC ............ *A61N 2/008* (2013.01); *A01G 7/04* (2013.01); *A01G 7/045* (2013.01); *A61B 5/242* (2021.01); *A61N 1/10* (2013.01); *A61N 5/0613* (2013.01)

(58) Field of Classification Search
CPC ........ A61N 2/008; A61N 1/10; A61N 5/0613; A01G 7/04; A01G 7/045
(Continued)

(56) References Cited

U.S. PATENT DOCUMENTS 5,895,298 A 4/1999 Faupel et al.
6,351,666 B1 2/2002 Cuzick et al.
(Continued)

FOREIGN PATENT DOCUMENTS

EP 0460670 11/1991
SI 21084 6/2003

OTHER PUBLICATIONS

Kaufmann Alain, Ridel Pauline. The affair of the memory of water. Towards a sociology of scientific communication. In: Réseaux. The French journal of communication, vol. 2, n2, 1994. pp. 183-204; doi: https://doi.org/10.3406/reso.1994.3277 (attached) (Year: 1994).*
(Continued)

*Primary Examiner* — Sunita Reddy
(74) *Attorney, Agent, or Firm* — Kanika Radhakrishnan; Evergreen Valley Law Group

(57) ABSTRACT

Embodiments of the present disclosure provide a biofield apparatus. The apparatus includes a first vial and a second vial configured to hold fluid for storing biofield information associated with a subject. The apparatus includes an input plate and an output plate. The input plate and the output plate include an input plate vial well and an output plate vial well, respectively. The apparatus includes a control unit configured to provide a first signal to the input plate for capturing the biofield information from the subject. The control unit encodes and transmits the biofield information captured from the subject, to the fluid within the first vial. Further, the control unit amplifies the biofield information within the first vial based on a target amplification level. The control unit transmits the biofield information from the fluid within the second vial to the subject for enhancing the biofield information and properties of the subject.

13 Claims, 7 Drawing Sheets

(51) Int. Cl.
*A01G 7/04* (2006.01)
*A61N 1/10* (2006.01)
*A61B 5/242* (2021.01)

(58) Field of Classification Search
USPC .................................................... 600/9–15
See application file for complete search history.

(56) References Cited

U.S. PATENT DOCUMENTS

| | | |
|---|---|---|
| 6,561,968 B1 | 5/2003 | Dissing et al. |
| 10,602,957 B2 | 3/2020 | Thomas |
| 2001/0051774 A1 | 12/2001 | Littrup et al. |
| 2002/0138099 A1* | 9/2002 | Markin ............... A61N 1/40 607/1 |
| 2009/0187232 A1* | 7/2009 | Salim ................. A61N 1/32 607/46 |
| 2013/0131537 A1* | 5/2013 | Tam ................... A61B 7/00 600/544 |
| 2016/0361416 A1 | 12/2016 | Taylor |
| 2017/0000379 A1* | 1/2017 | Thomas .............. A61B 5/055 |
| 2017/0007847 A1* | 1/2017 | Gross ................. A61M 21/02 |
| 2017/0326331 A1* | 11/2017 | Joseph ............... A61B 5/486 |
| 2018/0016196 A1* | 1/2018 | Choi .................. A01C 3/023 |
| 2020/0357488 A1 | 11/2020 | Truong et al. |
| 2021/0046184 A1 | 2/2021 | Martin |

OTHER PUBLICATIONS

Kafatos, Menas C .. et al. "Biofield science: current physics perspectives." Global advances in health and medicine 4.1 _suppl (2015): gahmj-2015.

* cited by examiner

BIOFIELD APPARATUS

TECHNICAL FIELD

The present disclosure relates to a biofield apparatus and, more particularly relates, to the biofield apparatus configured to collect, encode, amplify and refine biofield information associated with a host (e.g., living organisms and non-living things).

BACKGROUND

In recent times, biofield science has become an emerging field of study for alternative modalities, biophysics, biology, bio-agriculture, functional genomics, neuroscience, and psychoneuroimmunology and remedies. Biofield science deals with biofield information (or energy waves) that is emitted from a host (such as living organisms and non-living things) and surrounding the host. Conventionally, a user (such as an operator, a specialist or a practitioner) uses biofield devices to modify and/or manipulate the energy waves associated with the host such as the living organisms like plants, animals, humans etc., and the non-living things like soil, minerals, water, food etc. However, some limiting factors commonly associated with conventional biofield devices are that the biofield devices generally emit extrinsic frequencies onto the host, rather than using the frequencies emitted from the host. The frequencies from the conventional biofield devices are predetermined and/or are not based on the biofield information of the host. Moreover, the conventional devices do not have functionalities of inverting or infinitely amplifying and refining the biofield (i.e. the frequencies) of the host. Additionally, biofield therapy investigation is limited by an inability to quantify the therapeutic effect.

Therefore, there is a need for biofield systems to overcome one or more limitations stated above in addition to providing other technical advantages.

SUMMARY

Various embodiments of the present disclosure provide a biofield apparatus.

In an embodiment, a biofield apparatus is disclosed. The biofield apparatus includes a first vial and a second vial configured to hold fluid for storing biofield information associated with a subject. The biofield apparatus includes an input plate and an output plate. The input plate and the output plate include an input plate vial well and an output plate vial well, respectively. Each of the input plate vial well and the output plate vial well allows insertion of the first vial and the second vial therein. Further, the biofield apparatus includes a control unit configured to control capturing of the biofield information and output management of the biofield information. The control unit is configured to at least provide a first signal to the input plate for capturing the biofield information emanating from the subject. The control unit is configured to encode and transmit the biofield information captured from the subject, to the fluid contained in the first vial removably coupled to the output plate vial well. Further, the control unit is configured to amplify the biofield information contained in the fluid stored in the first vial based at least on a target amplification level. The amplification includes transferring the biofield information contained in the fluid of the first vial to the fluid contained in the second vial. The control unit is configured to transmit the biofield information from the fluid contained in the second vial to the subject, thereby enhancing the biofield information and one or more properties associated with the subject.

In another embodiment, a method of operating a biofield apparatus for managing biofield information associated with a subject is disclosed. The method performed by a control unit includes providing a first signal to an input plate for capturing the biofield information emanating from the subject. The method includes encoding and transmitting the biofield information captured from the subject, to a fluid contained in a first vial removably coupled to an output plate vial well. Further, the method includes amplifying the biofield information contained in the fluid stored in the first vial based at least on a target amplification level. The amplification includes transferring the biofield information contained in the fluid of the first vial to the fluid contained in a second vial. The method includes, upon amplification, transmitting the biofield information from the fluid contained in the second vial to the subject, thereby enhancing the biofield information and one or more properties associated with the subject.

In yet another embodiment, the biofield apparatus is disclosed. The biofield apparatus includes a first vial and a second vial configured to hold fluid for storing biofield information associated with a subject. The biofield apparatus includes an input plate and an output plate. The input plate and the output plate include an input plate vial well and an output plate vial well, respectively. Each of the input plate vial well and the output plate vial well allows insertion of the first vial and the second vial therein. Further, the biofield apparatus includes a control unit configured to control capturing of the biofield information and output management of the biofield information. The control unit is configured to at least provide a first signal to the input plate for capturing the biofield information emanating from the subject placed on the input plate. The control unit is configured to encode and transmit the biofield information captured from the subject, to the fluid contained in the first vial removably coupled to the output plate vial well. Further, the control unit is configured to amplify and refine the biofield information contained in the fluid stored in the first vial based at least on a target amplification level. The amplification includes transferring the biofield information within the fluid contained in the first vial between the first vial and the second vial until the target amplification level is reached. The biofield information is transmitted between the fluid contained in the first vial and the fluid contained in the second vial, when the first vial and the second vial are removably coupled to the input plate vial well and the output plate vial well, respectively. The control unit is configured to transmit the biofield information stored in the fluid contained in the first vial to the subject for enhancing the biofield information and the one or more properties associated with the subject.

BRIEF DESCRIPTION OF THE FIGURES

The following detailed description of illustrative embodiments is better understood when read in conjunction with the appended drawings. For the purpose of illustrating the present disclosure, exemplary constructions of the disclosure are shown in the drawings. However, the present disclosure is not limited to a specific device or a tool and instrumentalities disclosed herein. Moreover, those in the art will understand that the drawings are not to scale. Wherever possible, like elements have been indicated by identical numbers.

Figure 1A:
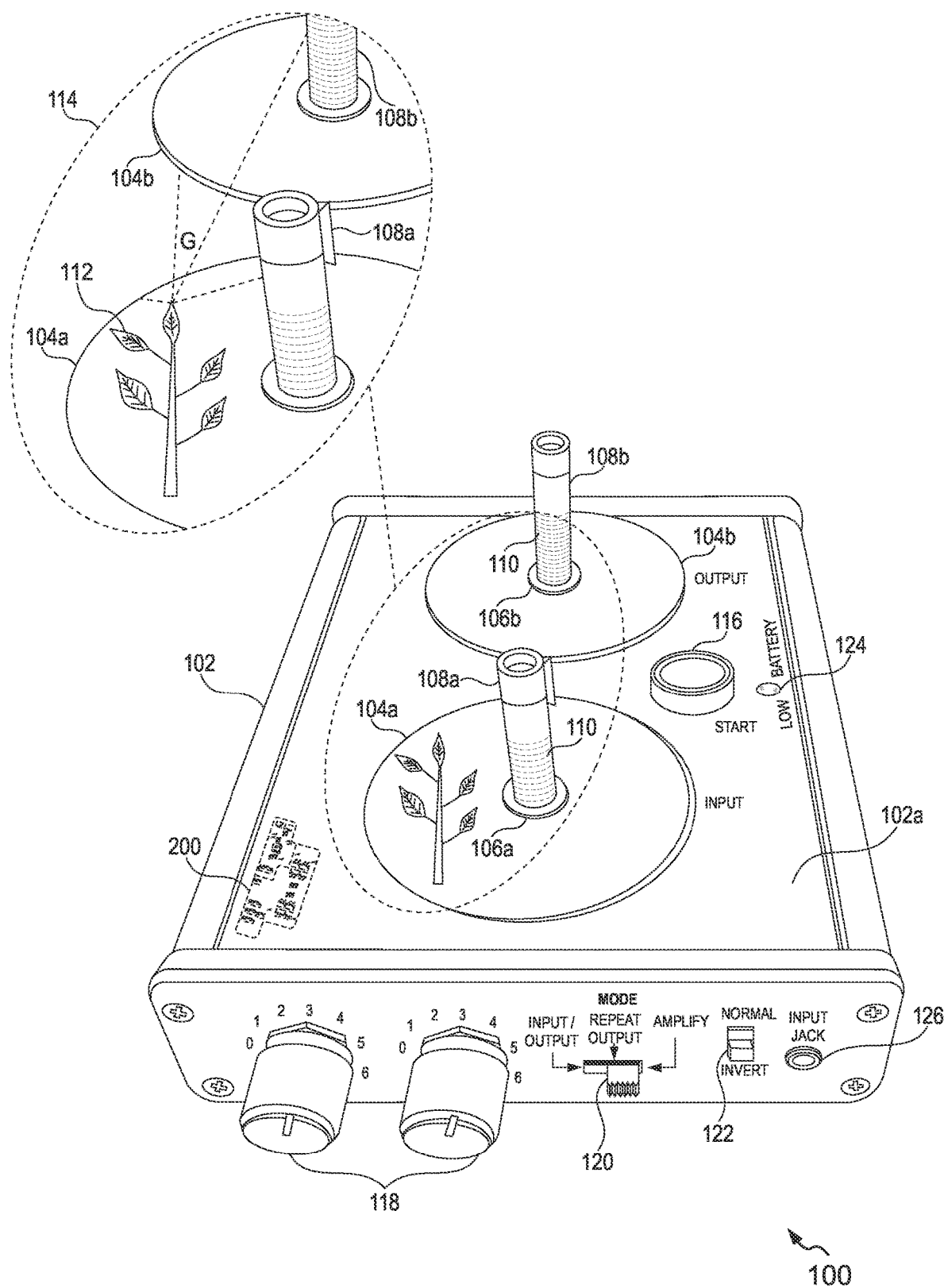
FIG. 1A illustrates a perspective view of a biofield apparatus, in accordance with an example embodiment of the present disclosure.

The drawings referred to in this description are not to be understood as being drawn to scale except if specifically noted, and such drawings are only exemplary in nature.

DETAILED DESCRIPTION

In the following description, for purposes of explanation, numerous specific details are set forth in order to provide a thorough understanding of the present disclosure. It will be apparent, however, to one skilled in the art that the present disclosure can be practiced without these specific details. Descriptions of well-known components and processing techniques are omitted to not obscure the embodiments herein unnecessarily. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Reference in this specification to "one embodiment" or "an embodiment" means that a particular feature, structure, or characteristic described in connection with the embodiment is included in at least one embodiment of the present disclosure. The appearances of the phrase "in an embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not for other embodiments.

Moreover, although the following description contains many specifics for the purposes of illustration, anyone skilled in the art will appreciate that many variations and/or alterations to said details are within the scope of the present disclosure. Similarly, although many of the features of the present disclosure are described in terms of each other, or in conjunction with each other, one skilled in the art will appreciate that many of these features can be provided independently of other features. Accordingly, this description of the present disclosure is set forth without any loss of generality to, and without imposing limitations upon, the present disclosure.

The terms "biofield information", and "bio-photons" and "biofields" are interchangeably used throughout the description. The biofield information, or the bio-photons or the biofields generally refers to spatially-distributed fields (or energy waves) that living systems emit and as well as which surrounds the living systems.

Overview

Various example embodiments of the present disclosure provide a biofield apparatus and a method of use. In an embodiment, the biofield apparatus includes a first vial and a second vial configured to hold fluid for storing biofield information associated with a subject. The biofield apparatus further includes an input plate and an output plate. The input plate and the output plate include an input plate vial well and an output plate vial well, respectively. Each of the input plate vial well and the output plate vial well allow insertion of the first vial and the second vial therein. The apparatus includes a control unit configured to control capturing of the biofield information and output management of the biofield information. The control unit is configured to provide a first signal to the input plate for capturing the biofield information emanating from the subject placed on the input plate. The control unit is configured to encode the biofield information and transmit the biofield information to the first vial that is removably coupled to the output plate vial well. Upon encoding, the first vial is detached from the output plate vial well and placed into the input plate vial well and the second vial is placed into the output plate vial well. Thereafter, the control unit is configured to amplify and refine the biofield information contained in the fluid stored in the first vial based at least on a target amplification level. The amplifying and refining process includes transferring the biofield information within the fluid contained in the first vial between the first vial and the second vial until the target amplification level is reached. Upon completion of amplification and refining, the control unit provides a second signal to the input plate and the input plate vial well. The second signal enables the amplified and refined biofield information within the fluid contained in the first vial secured to the input plate vial well to be transmitted to the subject placed on the output plate, for enhancing the biofield information and one or more properties associated with the subject. In an embodiment, the apparatus includes a plurality of probes connected to the apparatus and placed onto the subject for collecting the biofield information from the subject and transmitting the amplified, encoded and refined biofield information to the subject.

Various embodiments of the present invention are described hereinafter with reference to FIGS. 1A-1D to FIG. 4.

Figure 1B:
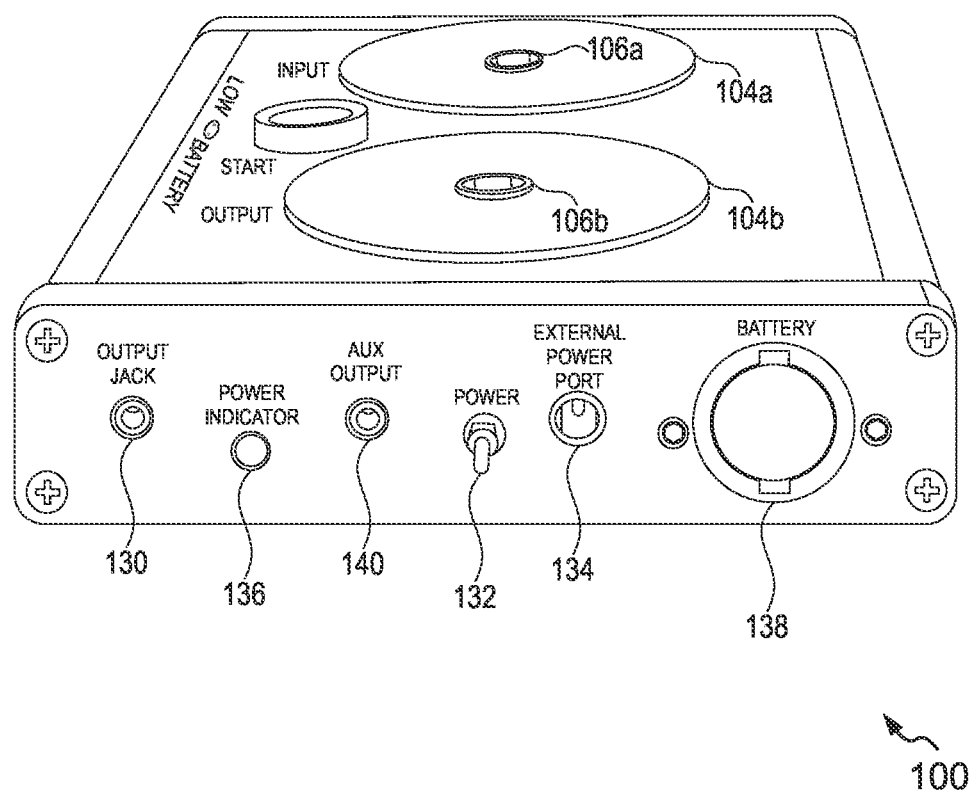
FIG. 1B illustrates another perspective view of the biofield apparatus, in accordance with an example embodiment of the present disclosure.

FIGS. 1A and 1B illustrate a perspective of a biofield apparatus 100, in accordance with an example embodiment of the present disclosure. The biofield apparatus 100 includes one or more components for collecting, encoding, amplifying and refining biofield information associated with a subject 112 (exemplarily depicted to be 'a plant'). Generally, the biofield apparatus 100 is used to perform biofield therapies which have impact on multiple dimensions of the subject and are expressed in quantum level matrix or electromagnetism or any other modulating means.

Particularly, the biofield physiology deals with electromagnetic, bio-photonic or bio-photons, and other types of spatially-distributed fields (or energy waves) that living systems (e.g., the subject 112) generate and respond to as integral aspects of subatomic particles (or bio-photons) such as cellular, tissue, and the like. In other words, the biofield information (or bio-photons) is an energy blueprint that corresponds to an entire organism (e.g., the subject 112). As such, the biofield information or the biofields can be perceived as affecting physiological regulatory systems of the organism (such as the subject 112) in a manner that conforms to molecular-based mechanisms. Further, the complex matrix associated with the biofield information connects physical, emotional, and mental dimensions of the subject 112. The biofields or the bio-photons are captured by the biofield apparatus 100 (hereinafter interchangeably referred to as "the apparatus 100") for performing biofield therapies (or for therapeutic purposes) which is herein explained further in detail As explained above, the apparatus 100 operates through a variety of modalities (or operation modes). Some non-exhaustive examples of the modalities associated with the apparatus 100 may include electromagnetic field (EMF)-light, EMF-heat, EMF-nonthermal, electrical current, vibration and sound, physical and mechanical, intentionality and nonlocality, gas and plasma, and any other modes.

As shown in FIG. 1A, the apparatus 100 includes a housing 102. The housing 102 is dimensionally and structurally configured to support the one or more components of the apparatus 100. Further, the apparatus 100 includes an input plate 104a and an output plate 104b. The input plate 104a and the output plate 104b are secured to a top portion 102a of the housing 102. The input plate 104a includes an input plate vial well 106a. The output plate 104b includes an output plate vial well 106b. In an embodiment, the input plate 104a and the output plate 104b are configured in a circular shape. In an alternate embodiment, the input plate 104a and the output plate 104b may be in any other geometric shapes as per design feasibility and requirement. In another embodiment, the input plate vial well 106a and the output plate vial well 106b may be mounted with a light source (e.g., light-emitting diodes (LEDs)) (not shown in Figures) which may emit light during specific modes/functions. It should be noted that the input plate 104a and the output plate 104b secured to the apparatus 100 are separated by a predefined distance to allow for optimal functioning during the biofield therapy.

Further, each of the input plate 104a and the output plate 104b selectively receives the subject 112 during the biofield therapy. Particularly, the input plate 104a may be configured to receive the biofield information emitted from the subject 112, when the subject 112 is placed on the input plate 104a (see, enlarged portion 114). It should be understood that the subject 112 that readily fits onto the input plate 104a and the output plate 104b is selectively placed on the input plate 104a and the output plate 104b during the biofield process which will be explained further in detail. Further, the output plate 104b may be configured to transfer the encoded, amplified and refined biofield information to the subject 112, when the subject 112 is placed on the output plate 104b. The subject 112 may include living organisms (e.g., humans, animals, plants, etc.), non-living things (e.g., water, soil, minerals, food, etc.), area of interest of the living organisms (e.g., elbow and knee of a human being), and area of interest of the non-living things (e.g., a side of a mineral).

In an embodiment, the input plate 104a and the output plate 104b may be made of materials that are capable of enabling interaction (i.e. exchanging of the biofield information) between the apparatus 100 and the subject 112. The biofield information associated with the subject 112 may be frequencies, magnetic fields, light, electrostatic information, and the like.

The apparatus 100 further includes a first vial 108a and a second vial 108b. The first vial 108a and the second vial 108b are configured to store and/or hold fluid 110 therein. Further, the input plate vial well 106a is configured to allow insertion of the first vial 108a or the second vial 108b therein. Similarly, the output plate vial well 106b is configured to allow insertion of the first vial 108a or the second vial 108b therein. The first vial 108a and the second vial 108b may be dimensionally configured in conformity to the dimensions of the input plate vial well 106a and the output plate vial well 106b for enabling insertion of the first vial 108a and the second vial 108b. It is noted that the first vial 108a or the second vial 108b are positioned perpendicular to the input plate vial well 106a or the output plate vial well 106b when either of the first vial 108a or the second vial 108b is removably coupled to the input plate vial well 106a or the output plate vial well 106b.

As explained above, the first vial 108a and the second vial 108b contain fluid 110. The fluid 110 serves as a medium to collect and hold the biofield information. More specifically, the fluid 110 contains memory which provides the tendency to hold the biofield information. The fluid 110 may be distilled water, filtered spring water, mineralized water, and/or structured water, medical-grade silica suspended in water, medical-grade sterile cotton suspended in water and other additives and liquids to enhance the encoding of the biofields. Similar to the input plate 104a and the output plate 104b, the first vial 108a and the second vial 108b may be made of materials that are capable of enabling interaction (i.e. exchanging of the biofield information) between the apparatus 100 and the subject 112.

It should be noted that the input plate 104a, the output plate 104b and the first and second vials 108a, 108b are coupled to the subject 112 through galvanic and/or capacitive connection along with photo detection for receiving and transmitting the biofield information. The galvanic connection 'G' among the input plate 104a, the output plate 104b, the first and second vials 108a, 108b and the subject 112 is represented as dotted lines (see, the enlarged portion 114). The galvanic connection 'G' is also referred to as galvanic isolation i.e. no direct electrical connection (or conductive path) between the two entities. This connection (i.e. the galvanic connection 'G') facilitates the electrical signal, in the presence of magnetic field and water (i.e. the fluid 110), conveys low frequency information below the noise level. This information is nevertheless present and subject to amplification, and the apparatus 100 does not identify these frequencies and transmits them with all complexities intact.

Further, the apparatus 100 includes a start button 116, one or more amplification knobs 118, a mode switch 120, a function switch 122, a low battery light-emitting diode (LED) indicator 124, an input jack 126, an output jack 130, a power switch 132, an external power port 134, a power-on LED indicator 136, a battery 138, and an auxiliary output jack 140. Each of the aforementioned components of the apparatus 100 is secured to the housing 102.

The start button 116 is configured to initiate the transfer of the biofield information emitted from the subject 112 into the fluid 110 contained in the first vial 108a. Subsequently, the start button 116 facilitates transfer of the biofield information collected and amplified between the fluid 110 contained in the first vial 108a and the fluid 110 contained in the second vial 108b. Further, transferring the amplified biofield information stored in the fluid 110 within the second vial 108b, to the subject 112. The process involved throughout the biofield process is further explained in detail with reference to FIG. 3.

The amplification knobs 118 include a suitable logic and circuitry, and are configured to allow a user (for example, an operator, a specialist, practitioners or a clinician etc.,) to select and/or adjust the degree of amplification to which the biofield information needs to be amplified. In other words, the user sets a target amplification level for amplifying the biofield information (e.g., frequencies) of the subject 112 by adjusting the amplification knobs 118 in the apparatus 100. The amplification knobs 118 are exemplarily depicted to be rotary knobs which allow the user to rotate the knobs 118 to set the target amplification level. As such, each knob (i.e. the knobs 118) may be rotated between a range of 0 to 9 to set the target amplification level in such a way that unlimited/infinite amplification of the biofield information is attained during the amplification process.

The mode switch 120 includes a suitable logic and circuitry that is configured with multiple operating modes such as, an input/output mode, a repeat output mode and an amplify mode. The mode switch 120 configured with the aforementioned operating modes allows the user to adjust a direction of transmission of the biofield information during use which will be explained further in detail. The mode switch 120 is exemplarily depicted to be a toggle switch which is configured to toggle between the operating modes associated with the mode switch 120.

The function switch 122 includes a suitable logic and circuitry configured with multiple function settings such as a normal function and an invert function. The normal function allows the apparatus 100 to collect, amplify and transfer the biofield information emitted from the subject 112 during any of the operating mode (i.e. the input/output mode or the repeat output mode or the amplify mode) selected in the mode switch 120. The invert function allows the apparatus 100 to transfer the collected, amplified and refined biofield information to the subject 112 in an inverted form under specific circumstances only (i.e. during selection of the repeat output mode in the mode switch 120). Similar to the mode switch 120, the function switch 122 is exemplarily depicted to be the toggle switch which is configured to toggle between the normal function and the invert function associated with the function switch 122.

The power switch 132 is configured to control electrical communication within the apparatus 100. The power switch 132 is exemplarily depicted to be a toggle switch which is configured to toggle between 'ON' and 'OFF' for allowing the electricity to flow through the circuitry for operating the apparatus 100. Further, the power-on LED indicator 136 is configured to emit light to alert the user such as the operator when the biofield apparatus 100 is turned ON. Moreover, the external power port 134 is configured to receive an external power source (not shown in Figures) to supply electrical energy for operating the apparatus 100 when the battery source (i.e. the battery 138) is not selected for providing power supply in the apparatus 100.

In an example scenario, the battery 138 may be a rechargeable battery, thus in this scenario, the power received from the external electrical source (not shown in Figures) may be stored in the battery 138. Thus, the battery 138 can be used as an alternative electrical energy supply for operating the biofield apparatus 100. During use, if the stored electrical energy in the battery 138 is determined to be low, the low battery LED indicator 124 emits light to alert the user about the low battery level. As such, the user may change the battery 138 in case of non-rechargeable batteries (e.g., AA batteries) or may recharge the battery 138 in case of the rechargeable batteries as explained above.

The auxiliary output jack 140 is configured to allow the connection to an auxiliary device (such as a low level laser, a light wand or any other device) for allowing transmission of the collected, refined, and amplified signal from the biofield apparatus 100 to the subject 112 through the auxiliary device. Further, the auxiliary output jack 140 is configured to allow the connection of an external storage device (not shown in Figures) to the biofield apparatus 100 for transmitting the collected, and amplified biofield information to the external storage device.

Figure 1C:
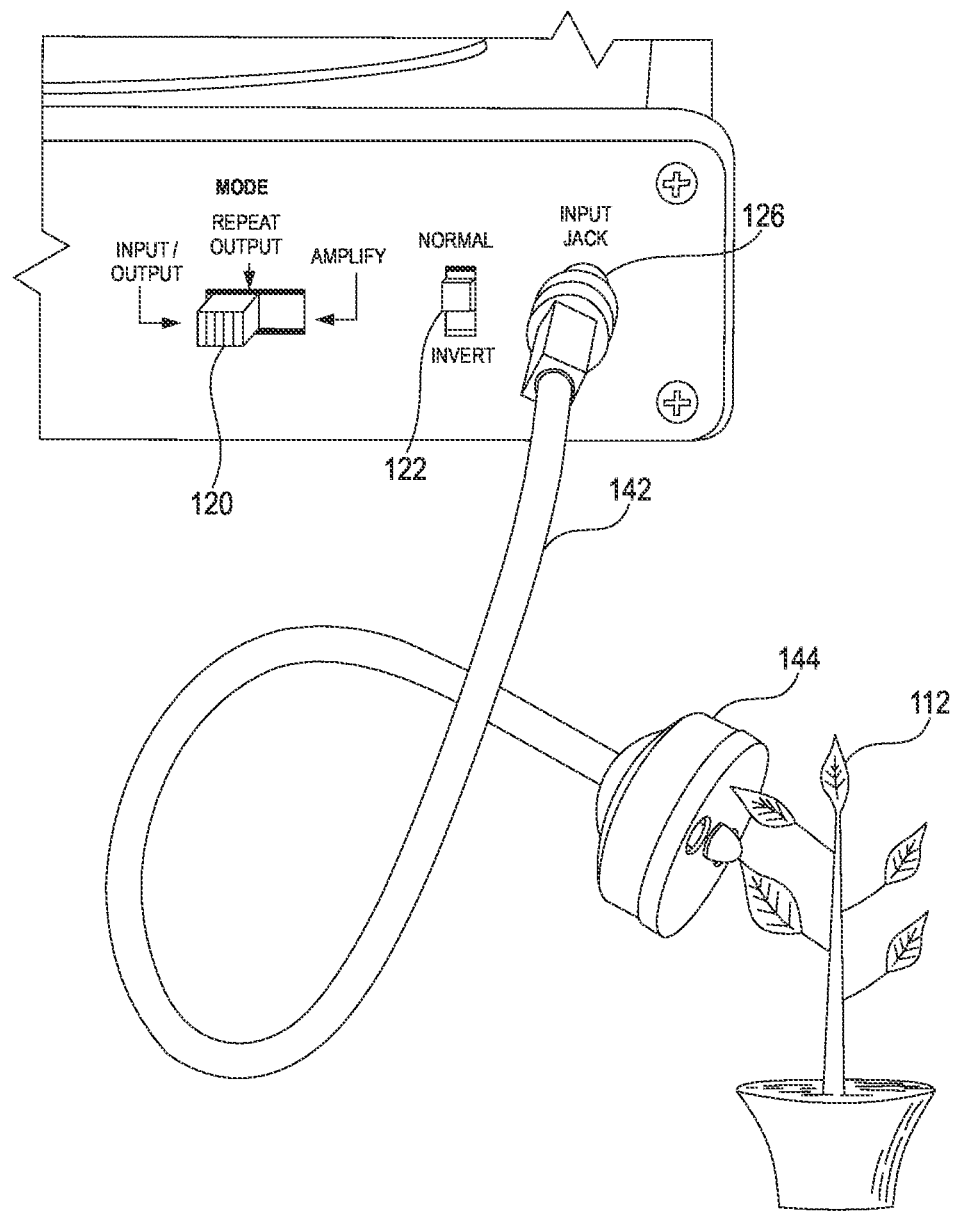
FIG. 1C illustrates a sectional view of the biofield apparatus of FIG. 1A, depicting a probe connected to an input jack of the biofield apparatus, in accordance with an example embodiment of the present disclosure.
Figure 1D:
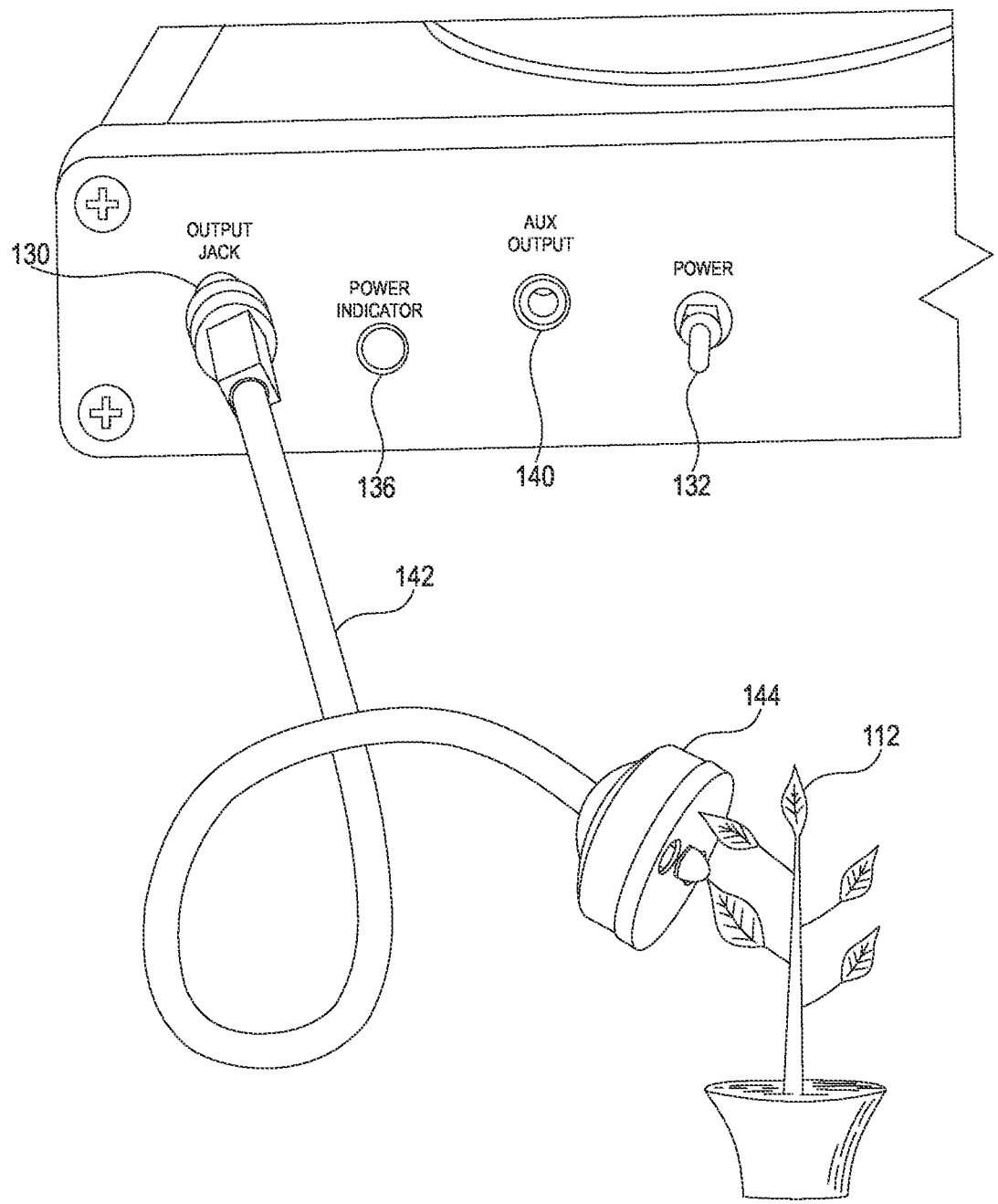
FIG. 1D illustrates a sectional view of the biofield apparatus of FIG. 1B, depicting the probe connected to an output jack of the biofield apparatus, in accordance with an example embodiment of the present disclosure.

The input jack 126 and the output jack 130 are configured to receive a plurality of probes 142 (as shown in FIGS. 1C and 1D). Generally, the probes 142 are configured to enable transmission of the biofield information between the apparatus 100 and the subject 112, when the subject 112 (exemplarily depicted to be a 'potted plant') does not readily fit onto the input plate 104a or the output plate 104b or a combination thereof. More specifically, the probe 142 includes a probe face 144. As shown in FIGS. 1C and 1D, the probe 142 is plugged into the input jack 126 and the output jack 130 and the probe face 144 is placed onto or against the subject 112. In an embodiment, the probe face 144 may include a light source which when plugged into the output jack 130 emits light in output mode and repeat output mode. The probe 142 inserted to the input jack 126 and the output jack 130, and the probe face 144 placed onto the subject 112 is configured to capture and/or collect the biofield information emanating from the subject 112 and transfer the amplified and refined biofield information to the subject 112. Further, collecting and transferring the biofield information from/to the subject 112 using the probes 142 connected to the input jack 126 and the output jack 130 are explained with reference to FIG. 3.

Further, the apparatus 100 includes a control unit 200 (represented using dotted lines in FIG. 1A) that is disposed within the housing 102. The control unit 200 is communicably coupled (either wired or wireless connection) to each of the start button 116, the amplification knobs 118, the mode switch 120, the function switch 122, the low battery LED indicator 124, the input jack 126, the output jack 130, the power switch 132, the external power port 134, the power-on LED indicator 136, the battery 138, and the auxiliary output jack 140 of the apparatus 100. The control unit 200 may include suitable logic and circuitry to collect, encode, amplify and refine the biofield information which is herein explained in detail with reference to FIG. 2. The components of the apparatus 100 explained herein may not be exhaustive and the apparatus 100 may include more or fewer components than those depicted and explained in FIGS. 1A-1D.

Figure 2:
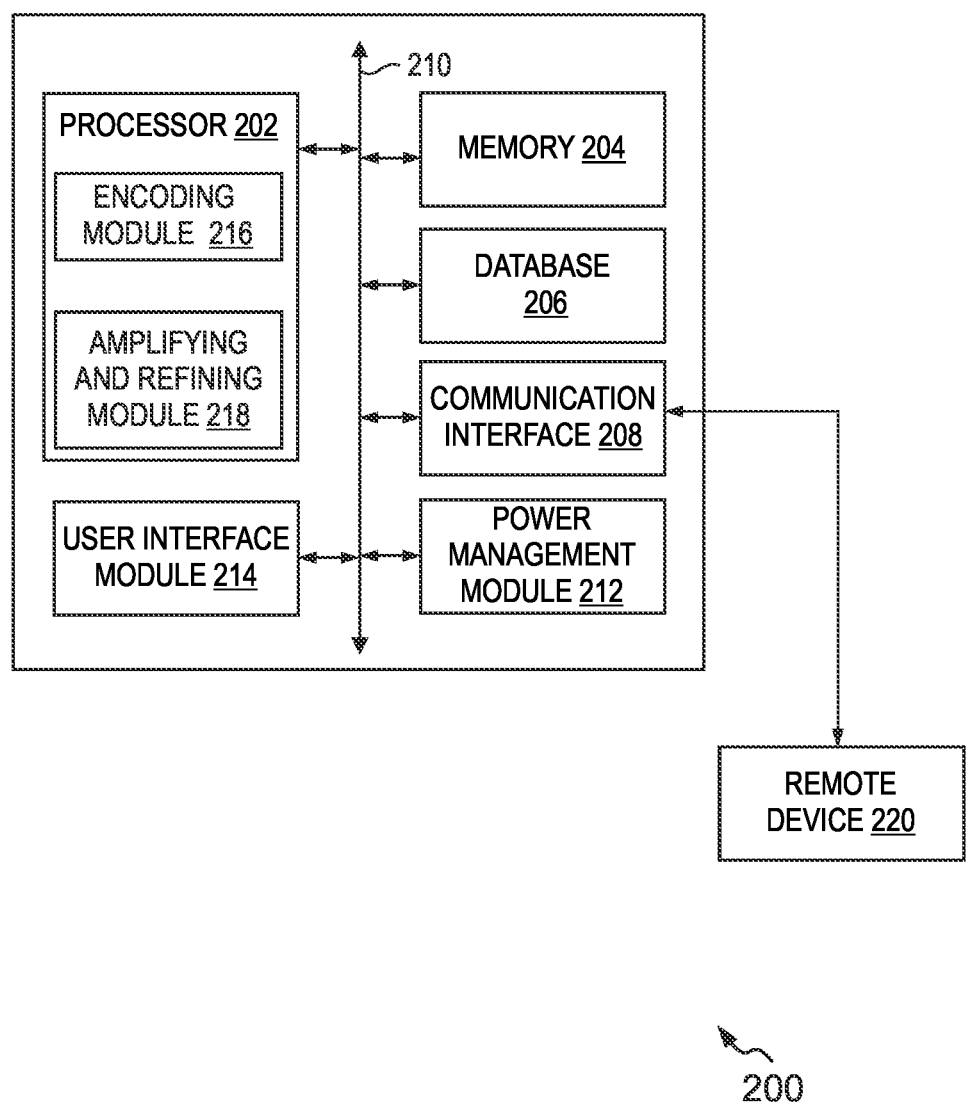
FIG. 2 illustrates a simplified block diagram representation of a control unit of the biofield apparatus, in accordance with an example embodiment of the present disclosure.

Referring to FIG. 2, a simplified block diagram representation of a control unit 200 is illustrated, in accordance with an example embodiment of the present disclosure. Further, the input plate 104a, the output plate 104b, and each of the first and second vials 108a and 108b are internally coupled to the control unit 200. As such, a main circuit board (not shown in Figures) may provide both electrical and mechanical foundation for such internal connections. It should be understood that the first and second vials 108a, 108b are connected to the control unit 200 when each of the first and second vials 108a, 108b is removably coupled to either of the input plate vial well 106a or the output plate vial well 106b. Further, coupling of the input and output plates 104a, and 104b and the first and second vials 108a, and 108b are facilitated by analog signal processing, magnetic fields, light, and electrostatic forces.

The control unit 200 includes at least one processor, such as a processor 202 and a memory 204. It is noted that although the control unit 200 is depicted to include only one processor, the control unit 200 may include more number of processors therein. In an embodiment, the memory 204 is capable of storing executable instructions. Further, the processor 202 is capable of executing the platform instructions to perform the operations described herein. In an embodiment, the processor 202 may be embodied as a multi-core processor, a single core processor, or a combination of one or more multi-core processors and one or more single core processors.

The memory 204 includes suitable logic, circuitry, and/or interfaces to store a set of computer readable instructions for performing operations described herein. The memory 204 may be embodied as one or more volatile memory devices, one or more non-volatile memory devices, and/or a combination of one or more volatile memory devices and non-volatile memory devices. Examples of the memory 204 include a random-access memory (RAM), a read-only memory (ROM), a removable storage drive, and the like. In at least some embodiments, the memory 204 stores instructions for enabling the processor 202 to collect, encode, amplify and refine the biofield information of a subject (e.g., the subject 112).

In one embodiment, the control unit 200 may include a database 206 that is configured to store the collected, encoded, amplified and refined biofield information.

The control unit 200 further includes a communication interface 208. The communication interface 208 may include communication circuitry such as for example, a transceiver circuitry and other communication media interfaces to connect to wired and/or wireless components associated with the apparatus 100. The communication circuitry may, in at least some example embodiments, enable transmission of biofield information to a remote device 220. The remote device 220 may be an external storage device that may be connected to the apparatus 100 through the auxiliary output jack 140. As such, the communication interface 208 allows transmission of the biofield information to the external storage device through a connection between the auxiliary output jack 140 and the remote device 220. The communication interface 208 may be configured to transmit and/or receive signals to/from other components of the apparatus 100. Additionally, the one or more components of the control unit 200 communicate with each other via a centralized circuitry system 210.

Further, the control unit 200 includes a power management module 212. The power management module 212 includes suitable logic and circuitry for managing the power supply to the control unit 200 and other components of the apparatus 100 for operating the apparatus 100. More specifically, the power management module 212 is configured to monitor the power supply at the external power port 134 and the power supply from the battery 138. The power management module 212 may transmit data related to state of charge (SoC) of the battery 138 and power supply at the external power port 134 to the processor 202. The processor 202 is configured to allow power supply from either the external power supply connected to the external power port 134 and the battery 138 during use. In one scenario, if the SoC of the battery 138 is determined to be low, the processor 202 is configured to turn 'ON' the LED indicator 124 for alerting the user to charge the battery 138.

The control unit 200 includes a user interface module 214. The user interface module 214 includes suitable logic and circuitry configured to receive signals from the one or more components of the apparatus 100 and transmit the signals to the processor 202 for enabling the processor 202 for performing one or more operations described herein. More specifically, the user interface module 214 may include a circuitry and/or interfaces connected to each of the amplification knobs 118, the mode switch 120 and the function switch 122. The user interface module 214 is configured to receive the information related to the target amplification level based on adjusting the amplification knobs 118. Further, the user interface module 214 receives the information related to the operating modes (either the input/output mode, the repeat output mode, or the amplify mode) and the function settings (either the normal or invert functions) based on adjusting the mode switch 120 and the function switch 122, respectively. Thereafter, the user interface module 214 transmits the information related to the target amplification level, the operating mode, and the function setting to the processor 202.

In one embodiment, the processor 202 includes an encoding module 216, and an amplifying and refining module 218.

The encoding module 216 includes suitable logic, circuitry and/or interfaces for encoding the biofield information captured from the subject 112. Prior to encoding, the processor 202 is configured to transmit a first signal to the input plate 104a. The first signal enables the input plate 104a to receive the biofield information emanating from the subject 112. It should be noted that the first signal is provided to the input plate 104a when the mode switch 120 is adjusted to the input/output mode. Upon collecting the biofield information, the encoding module 216 is configured to transfer and/or encode the collected biofield information emitted from the subject 112 to the fluid 110 contained in the first vial 108a. In one example, the encoding module 216 may be an encoder device configured to encode the biofield information collected from the subject 112 to the fluid 110 contained in the first vial 108a.

The amplifying and refining module 218 includes suitable logic, circuitry and/or interfaces for amplifying the biofield information in order to enhance the biofield information and one or more properties of the subject 112. It should be noted that the amplifying and refining module 218 is configured to amplify and refine the biofield information encoded to the fluid 110 contained in the first vial 108a based on adjusting the mode switch 120 to amplify mode. The amplifying and refining module 218 is configured to amplify the biofield information stored in the fluid 110 contained in the first vial 108a by transferring the biofield information to the fluid 110 contained in the second vial 108b. For further refining the biofield information, the amplifying and refining module 218 transmits the biofield information between the fluid 110 contained in the second vial 108b and the fluid 110 contained in the first vial 108a until the target amplification level is reached.

Upon completing the amplification and refinement process, the processor 202 is configured to provide a second signal to the first vial 108a. The second signal enables transferring of the amplified biofield information stored in the fluid 110 contained in the first vial 108a to the subject 112, thereby enhancing the biofield information and one or more properties of the subject 112. The output (i.e. the biofield information) of the apparatus 100 may be transmitted to the subject 112 and create subsequent change in the subject 112. For instance, the subject 112 can be taken as soil. The apparatus 100 is configured to collect the biofield information from the subject 112, amplify and refine the biofield information and transmit the modified biofield information to the subject 112. As such, the amplified biofield information may improve robustness of the soil against invasive species (e.g., weeds, biotic stress etc.). In an example, the apparatus 100 may receive food as the subject 112 to improve and enhance the taste of food. In another example, the subject 112 may be a human being who is suffering from elbow joint pain. As such, the apparatus 100 may collect the biofield information from the elbow of the subject 112 and amplify the biofield information to perform therapeutic procedure on the elbow joint for relieving the pain in the elbow joint.

In one example scenario, the target amplification level may be reached in the amplification process i.e. when the biofield information from the fluid 110 contained in the first vial 108a is transmitted to the fluid 110 contained in the second vial 108b. In this scenario, upon completion of the amplification and refining process, the second vial 108b is removed from the output plate vial well 106b and is placed into the input plate vial well 106a. Thereafter, the processor 202 may provide the second signal to the input plate 104a to transmit the biofield information stored in the fluid 110 contained in the second vial 108b to the subject 112 placed on the output plate 104b.

Figure 3:
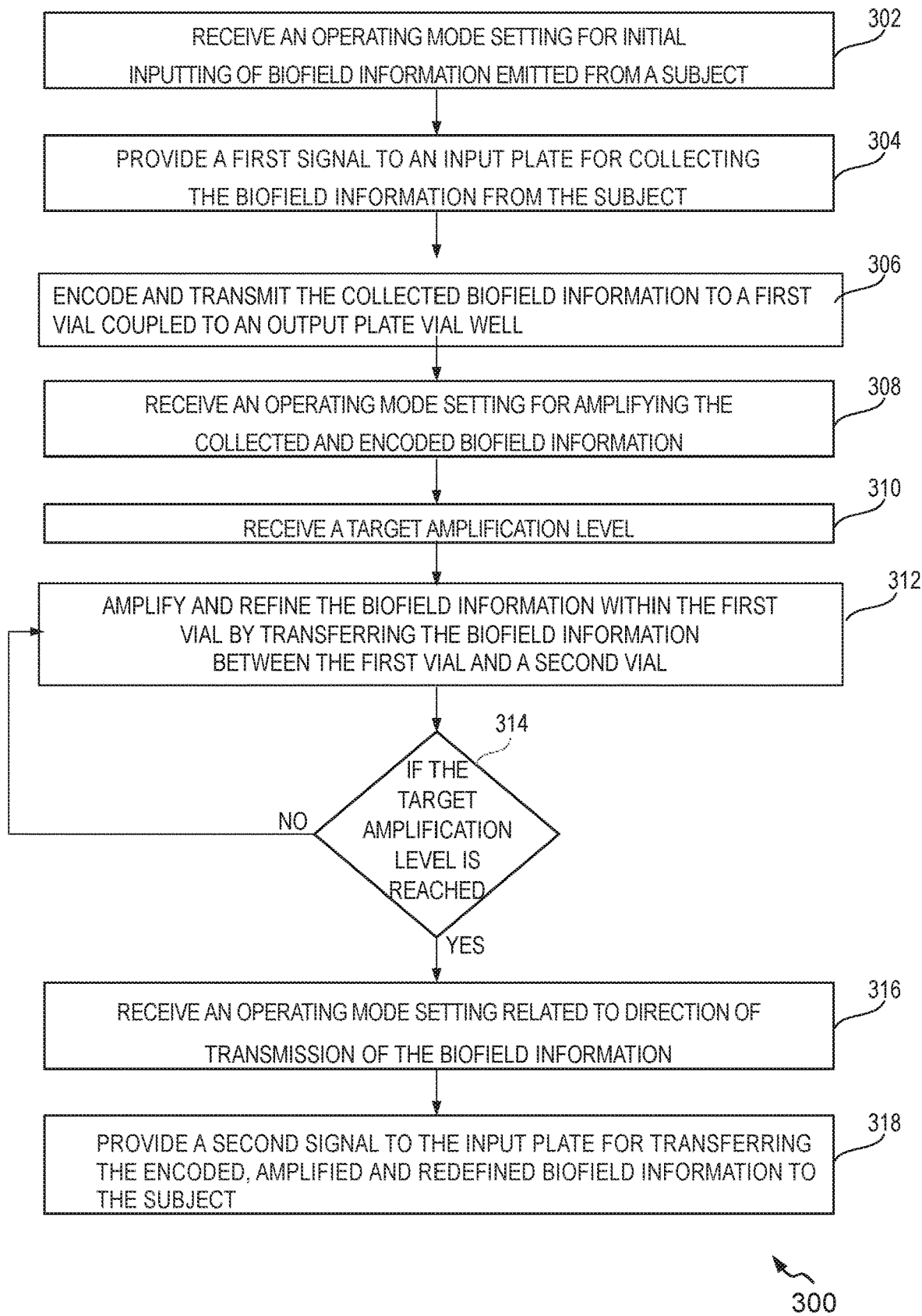
FIG. 3 represents a flow chart for a process flow for operating the biofield apparatus to collect, encode, amplify and refine biofield information, in accordance with an example embodiment of the present disclosure.

FIG. 3 represents a flow chart 300 for a process flow for operating the biofield apparatus 100 to collect, encode, amplify and refine the biofield information, in accordance with an example embodiment of the present disclosure. It should be appreciated that one or more operations explained in the flow chart 300 is performed by the control unit 200. The steps of the flow chart 300 are performed when the biofield apparatus 100 is operated for collecting, encoding, amplifying and refining the biofield information. The sequence of operations of the flow chart 300 may not be necessarily executed in the same order as they are presented. Further, one or more operations may be grouped together and performed in form of a single step, or one operation may have several sub-steps that may be performed in parallel or in a sequential manner. It should be appreciated that the steps of the flow chart 300 are executed when the function switch 122 is selected to be the normal function setting. The process starts at 302.

At 302, the control unit 200 receives an operating mode setting for initial inputting of biofield information emitted from a subject (e.g., the subject 112). During use, the subject 112 is placed on the input plate 104a (as shown in FIG. 1A). In an embodiment, the subject 112 may not readily fit onto the input plate 104a and the output plate 104b. In this case, the probe 142 is connected to the input jack 126 and the probe face 144 is placed onto the subject 112 (as shown in FIG. 1C). Thereafter, the user selects the input/output mode using the mode switch 120, and the first vial 108a filled with the fluid 110 is inserted into the output plate vial well 106b. Based on selecting the input/output mode, the user interface module 214 transmits the operation mode setting to the control unit 200 for initiating the biofield process. In this scenario, the amplification knobs 118 are set to zero reading.

At 304, the control unit 200 provides a first signal to an input plate for collecting the biofield information from the subject. More specifically, the control unit 200 provides the first signal to the input plate 104a based on pressing the start button 116, upon placing the subject 112 on the input plate 104a, and setting the operating mode to the input/output mode and the amplification knobs to zero reading. The first signal enables the input plate 104a to collect or capture the biofield information emanating from the subject 112. Similarly, the probe 142 connected to the input jack 126 collects the biofield information emitting from the subject 112 based on receipt of the first signal at the input jack 126.

At 306, the control unit 200 encodes and transmits the biofield information captured from the subject to a first vial coupled to an output plate vial well. The biofield information is encoded and transmitted to the fluid 110 contained in the first vial 108a removably coupled to the output plate vial well 106b.

Additionally, the user (such as the operator or the specialist) may wish to reposition the subject 112 placed on the input plate 104a for collecting the biofield information of the subject 112 in a newly positioned state of the subject 112. In this scenario, the user may reposition the subject 112 on the input plate 104a and repress the start button 116, and the steps 304, 306 are repeated to collect the biofield information of the subject 112 in the newly positioned state, and encode and transmit the biofield information to the first vial 108a. Similarly, the probe 142 may be repositioned on the subject 112 for capturing and encoding the biofield information as explained above. Upon encoding the biofield information to the fluid 110 contained in the first vial 108a, the subject 112 is removed from the input plate 104a. In a similar manner, the probe 142 is disconnected from the input jack 126, upon encoding process.

At 308, the control unit 200 receives an operating mode setting for amplifying the collected and encoded biofield information. For amplification, the mode switch 120 is set to the amplify mode, and the first vial 108a is decoupled from the output plate vial well 106b and inserted to the input plate vial well 106a, and the second vial 108b is inserted into the output plate vial well 106b. Further, the control unit 200 receives a target amplification level (see, 310). The target amplification level is set by adjusting the amplification knobs 118.

At 312, the control unit 200 amplifies and refines the biofield information within the first vial, by transferring the biofield information between the first vial and a second vial. At 314, the control unit 200 checks if the target amplification level is reached, upon amplifying and refining the biofield information by transferring between the first vial 108a and the second vial 108b. If the target amplification level is not reached, step 312 is performed which is explained further in detail.

In one scenario, the control unit 200 amplifies and refines the biofield information within the first vial 108a secured to the input plate vial well 106a and transfers the amplified and refined biofield information to the fluid 110 within the second vial 108b secured to the output plate vial well 106b. Thereafter, step 314 is performed, to check if the target amplification level is reached upon transferring the amplified and refined biofield information to the second vial 108b. Once the target amplification level is reached, step 316 is performed. In this scenario, the first vial 108a is removed from the input plate vial well 106a and the second vial 108b is transmitted to the input plate vial well 106a, as the amplified and refined biofield information is within the fluid 110 contained in the second vial 108b.

In another scenario, if the target amplification level is not reached, the step 312 is performed for further amplifying and refining the biofield information by transferring the biofield information back and forth between the first vial 108a and the second vial 108b, until the target amplification level is reached. In further amplification and refinement process, the biofield information is transmitted from the second vial 108b to the first vial 108a.

At 316, the control unit 200 receives an operating mode setting related to direction of transmission of the biofield information. The operating mode setting related to the direction of transmission of the biofield information is provided by using the mode switch 120. In one scenario, the user may choose to select the input/output mode on the mode switch 120 for non-continuous transmission of the biofield information from either of the first vial 108a or the second vial 108b to the subject 112 based on completion of the amplification and refining process. In another scenario, the user may choose to select the repeat output mode on the mode switch 120 for continuous transmission of the biofield information from either of the first vial 108a or the second vial 108b to the subject 112 based on completion of the amplification and refining process. In other words, the biofield information is transmitted to the subject 112 in at least a continuous manner and a non-continuous manner, based at least on receipt of the operating mode setting set using the mode switch 120. It will be apparent that the vial (either the first vial 108a or the second vial 108b) holding the highest amplification (i.e. the target amplification level) at the end of the amplification and refinement process is placed onto the input plate vial well 106a for transmission which is explained further in detail.

At 318, the control unit 200 provides a second signal to the input plate 104a for transferring the encoded, amplified and refined biofield information to the subject 112. The second signal is provided to the input plate 104a, upon pressing the start button 116. In one example scenario, the first vial 108a may contain the amplified, refined and encoded biofield information, and is secured to the input plate 104a as explained above. In this scenario, the second signal enables transmission (either continuous or non-continuous transmission) of the biofield information from the fluid 110 contained in the first vial 108a secured to the input plate vial well 106a to the subject 112 placed on the output plate 104b, thereby enhancing the biofield information and one or more properties associated with the subject 112. In another example scenario, the second vial 108b may contain the amplified, refined and encoded biofield information, and is secured to the input plate 104a as explained above. In this scenario, the second signal enables transmission of the biofield information from the second vial 108b to the subject 112 on the output plate 104b. It should be noted that the amplification knobs 118 are set to zero reading during the transmission (either continuous manner or the non-continuous manner) of the amplified, refined, and encoded biofield information stored in either the first vial 108a or the second vial 108b upon completion of the amplification and refining process, to the subject 112.

In a similar manner, the probe 142 is used to transmit the biofield information to the subject 112. In this case, the probe 142 is connected to the output jack 130 and the probe face 144 is placed onto the subject 112 (as shown in FIG. 1D). As such, the amplified, refined and encoded biofield information from either the first vial 108a or the second vial 108b coupled to the input plate vial well 106a is transmitted (either continuously or non-continuously) to the subject 112 through the probe 142 connected to the output jack 130.

Figure 4:
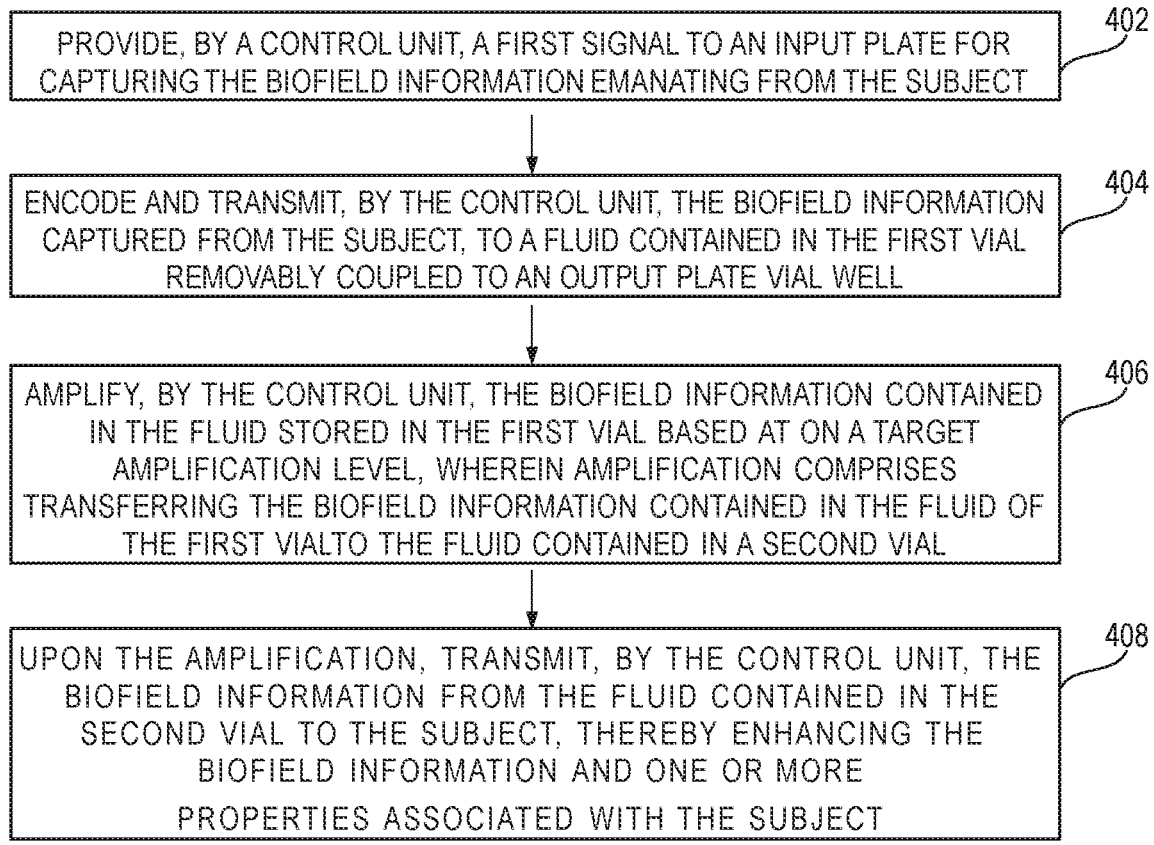
FIG. 4 illustrates a flow diagram of a method of operating the biofield apparatus for managing the biofield information, in accordance with an embodiment of the present disclosure.

FIG. 4 illustrates a flow diagram of a method 400 of operating the biofield apparatus 100 for managing biofield information associated with a subject, in accordance with an embodiment of the present disclosure. The method 400 depicted in the flow diagram may be executed by, for example, the control unit 200. The method 400 starts at operation 402.

At operation 402, the method 400 includes providing, by a control unit, a first signal to an input plate for capturing the biofield information emanating from the subject.

At operation 404, the method 400 includes encoding and transmitting, by the control unit, the biofield information captured from the subject, to a fluid contained in a first vial removably coupled to an output plate vial well.

At operation 406, the method 400 includes amplifying, by the control unit, the biofield information contained in the fluid stored in the first vial based at least on a target amplification level. The amplification includes transferring the biofield information contained in the fluid of the first vial to the fluid contained in a second vial.

At operation 408, the method 400 includes upon the amplification, transmitting, by the control unit, the biofield information from the fluid contained in the second vial to the subject, thereby enhancing the biofield information and one or more properties associated with the subject.

Further, collecting, encoding, amplifying and refining the biofield information by the control unit 200 of the biofield apparatus 100 are already explained in detail with reference to FIGS. 2 and 3, and they are not reiterated herein, for the sake of brevity.

Various embodiments of the disclosure, as discussed above, may be practiced with steps and/or operations in a different order, and/or with hardware elements in configurations, which are different than those which are disclosed. Therefore, although the disclosure has been described based upon these exemplary embodiments, it is noted that certain modifications, variations, and alternative constructions may be apparent and well within the spirit and scope of the disclosure.

Although various exemplary embodiments of the disclosure are described herein in a language specific to structural features and/or methodological acts, the subject matter defined in the appended claims is not necessarily limited to the specific features or acts described above. Rather, the specific features and acts described above are disclosed as exemplary forms of implementing the claims.

What is claimed is:

1. A biofield apparatus, comprising:
 a first vial and a second vial each configured to hold fluid for storing biofield information associated with a subject;
 an input plate and an output plate, the input plate and the output plate comprising an input plate vial well and an output plate vial well, respectively, wherein each of the input plate vial well and the output plate vial well allows insertion of the first vial and the second vial therein and wherein the input plate, the output plate, the first vial and the second vial are coupled to the subject through a galvanic connection with photo detection for receiving and transmitting the biofield information;
 a mode switch configured for selecting an input mode or an output mode by the user; and
 a control unit configured to control capturing of the biofield information emanating from the subject, output, and management of the biofield information, wherein the control unit comprising at least one processor capable of executing instructions and a memory capable of storing executable instructions is configured to:
  receive an operating mode setting for initial inputting of biofield information emitted from the subject using the mode switch, based on the selection of the input mode or output mode for initiating the biofield process and setting one or more amplification knobs of the biofield apparatus to zero reading and inserting the first vial filled with the fluid into the output plate vial well;

provide a first signal to the input plate for capturing the biofield information emanating from the subject galvanically coupled to the input plate, based on an user action received through a start button, the input plate or at least one probe adapted to be in contact with the subject, and wherein the at least probe connected to an input jack collects the biofield information emitting from the subject based on receipt of the first signal at the input jack, encode and transmit the biofield information captured from the subject through the galvanic connection, to the fluid contained in the first vial removably coupled to the output plate vial well, collect, encode and transmit the biofield information of the subject in a re-positioned state to the first vial by repositioning the at least one probe on the subject for capturing and encoding the biofield information, and removing the subject from the input plate and disconnecting the at least one probe from the input jack upon encoding process, receive an operating mode setting for amplifying the collected and encoded biofield information by setting the mode switch to an amplify mode and the first vial is decoupled from the output plate vial well and inserted to the input plate vial well, and the second vial is inserted into the output plate vial well, receive a target amplification level set by adjusting the one or more amplification knobs, amplify and refine the biofield information within the first vial, by transferring the biofield information back and forth between the first vial and the second vial connected through the galvanic connection until the set target amplification level is reached, and the first vial is removed from the input plate vial well and the second vial is transmitted to the input plate vial well after the set target amplification level is reached, transmit the biofield information to the subject in at least a continuous manner and a non-continuous manner, based at least on operating mode setting related to direction of transmission of the biofield information, the operating mode setting related to the direction of transmission provided using the mode switch, and provide a second signal to the input plate for transferring the encoded, amplified and refined biofield information to the subject, wherein the second signal is provided to the input plate based on the user action received through the start button, and the second signal enables continuous or non-continuous transmission of the biofield information from the fluid contained in the first vial or the second vial secured to the input plate vial well to the subject placed on the output plate through the galvanic connection, enhancing the biofield information by creating a subsequent change in the subject and the one or more amplification knobs are set to zero reading during the transmission.

2. The biofield apparatus as claimed in claim 1, wherein the biofield information associated with the subject comprises light information.

3. The biofield apparatus as claimed in claim 1, wherein the biofield information is transmitted from the fluid contained in the first vial to the fluid contained in the second vial and the first vial and the second vial are removably coupled to the input plate vial well and the output plate vial well, respectively.

4. The biofield apparatus as claimed in claim 1, wherein the biofield information stored in the fluid contained in the second vial is transmitted to the subject, with the second vial removably coupled to the input plate vial well and the subject galvanically coupled to the output plate, and wherein the biofield information from the fluid contained in the second vial is transmitted to the subject based upon receipt of a second signal at the input plate.

5. The biofield apparatus as claimed in claim 1, wherein the at least one probe is adapted to be in contact with the subject, wherein the at least one probe comprises a plurality of probes, wherein the plurality of probes is coupled to an input jack and an output jack of the biofield apparatus, and wherein the plurality of probes coupled to the input jack and the output jack is configured to be placed on the subject to capture the biofield information associated with the subject and to transmit the biofield information to the subject, respectively.

6. The biofield apparatus as claimed in claim 1, wherein the input plate, the output plate and the first and second vials are coupled to the subject through a galvanic connection.

7. A method of operating a biofield apparatus for managing biofield information associated with a subject, the method comprising:

storing biofield information associated with a subject in a first vial and a second vial each configured to hold fluid;

inserting the first vial and the second vial in an input plate vial well and an output plate vial well of an input plate and an output plate, respectively;

selecting an input mode or an output mode by the user using a mode switch;

receiving, by a control unit, an operating mode setting for initial inputting of biofield information emitted from the subject using the mode switch, based on the selection of the input mode or output mode for initiating the biofield process and setting one or more amplification knobs of the biofield apparatus to zero reading and inserting the first vial filled with the fluid into the output plate vial well;

providing, by a control unit, a first signal to an input plate for capturing the biofield information emanating from the subject galvanically coupled to the input plate, based on an user action received through a start button, the input plate or at least one probe adapted to be in contact with the subject, and wherein the at least probe connected to an input jack collects the biofield information emitting from the subject based on receipt of the first signal at the input jack;

encoding and transmitting, by the control unit, the biofield information captured from the subject through the galvanic connection, to a fluid contained in a first vial removably coupled to an output plate vial well;

collecting, encoding and transmitting, by the control unit, the biofield information of the subject in a re-positioned state to the first vial by repositioning the at least one probe on the subject for capturing and encoding the biofield information, and removing the subject from the input plate and disconnecting the at least one probe from the input jack upon encoding process;

receiving, by the control unit, an operating mode setting for amplifying the collected and encoded biofield information by setting the mode switch to an amplify mode and the first vial is decoupled from the output plate vial well and inserted to the input plate vial well, and the second vial is inserted into the output plate vial well;

receiving, by the control unit, a target amplification level set by adjusting the one or more amplification knobs;

amplifying and refining, by the control unit, the biofield information within the first vial, by transferring the biofield information back and forth between the first vial and the second vial connected through the galvanic connection until the set target amplification level is reached, and the first vial is removed from the input plate vial well and the second vial is transmitted to the input plate vial well after the set target amplification level is reached;

transmitting, by the control unit, the biofield information to the subject in at least a continuous manner and a non-continuous manner, based at least on operating mode setting related to direction of transmission of the biofield information, the operating mode setting related to the direction of transmission provided using the mode switch; and providing, by the control unit a second signal to the input plate for transferring the encoded, amplified and refined biofield information to the subject, wherein the second signal is provided to the input plate based on the user action received through the start button, and the second signal enables continuous or non-continuous transmission of the biofield information from the fluid contained in the first vial or the second vial secured to the input plate vial well to the subject placed on the output plate through the galvanic connection, enhancing the biofield information by creating a subsequent change in the subject and the one or more amplification knobs are set to zero reading during the transmission.

8. The method as claimed in claim 7, wherein the biofield information associated with the subject comprises light information.

9. The method as claimed in claim 7, wherein the biofield information is transmitted from the fluid contained in the first vial to the fluid contained in the second vial and the first vial and the second vial are removably coupled to an input plate vial well and the output plate vial well, respectively.

10. The method as claimed in claim 7, wherein the biofield information stored in the fluid contained in the second vial is transmitted to the subject, with the second vial removably coupled to an input plate vial well and the subject galvanically coupled to an output plate, and wherein the biofield information from the fluid contained in the second vial is transmitted to the subject based upon receipt of a second signal at the input plate.

11. A biofield apparatus, comprising:
a first vial and a second vial each configured to hold fluid for storing biofield information associated with a subject;
an input plate and an output plate, the input plate and the output plate comprising an input plate vial well and an output plate vial well, respectively, wherein each of the input plate vial well and the output plate vial well allows insertion of the first vial and the second vial therein and wherein the input plate, the output plate, the first vial and the second vial are coupled to the subject through a galvanic connection with photo detection for receiving and transmitting the biofield information;
a mode switch configured for selecting an input mode or an output mode by the user; and
a control unit configured to control capturing of the biofield information emanating from the subject, output, and management of the biofield information, the control unit comprising at least one processor capable of executing instructions and a memory capable of storing executable instructions is configured to:
receive an operating mode setting for initial inputting of biofield information emitted from the subject using the mode switch, based on the selection of the input mode or output mode for initiating the biofield process and setting one or more amplification knobs of the biofield apparatus to zero reading and inserting the first vial filled with the fluid into the output plate vial well;
provide a first signal to the input plate for capturing the biofield information emanating from the subject galvanically coupled to the input plate, based on an user action received through a start button, the input plate or at least one probe adapted to be in contact with the subject, and wherein the at least probe connected to an input jack collects the biofield information emitting from the subject based on receipt of the first signal at the input jack,
encode and transmit the biofield information captured from the subject through the galvanic connection, to the fluid contained in the first vial removably coupled to the output plate vial well,
collect, encode and transmit the biofield information of the subject in a re-positioned state to the first vial by repositioning the at least one probe on the subject for capturing and encoding the biofield information, and removing the subject from the input plate and disconnecting the at least one probe from the input jack upon encoding process,
receive an operating mode setting for amplifying the collected and encoded biofield information by setting the mode switch to an amplify mode and the first vial is decoupled from the output plate vial well and inserted to the input plate vial well, and the second vial is inserted into the output plate vial well,
receive a target amplification level set by adjusting the one or more amplification knobs,
amplify and refine the biofield information within the first vial, by transferring the biofield information back and forth between the first vial and the second vial connected through the galvanic connection until the set target amplification level is reached, and the first vial is removed from the input plate vial well and the second vial is transmitted to the input plate vial well after the set target amplification level is reached, wherein the biofield information is transmitted between the fluid contained in the first vial and the fluid contained in the second vial, with the first vial and the second vial removably coupled to the input plate vial well and the output plate vial well, respectively,
transmit the biofield information to the subject in at least a continuous manner and a non-continuous manner, based at least on operating mode setting related to direction of transmission of the biofield information, the operating mode setting related to the direction of transmission provided using the mode switch, and
provide a second signal to the input plate for transferring the encoded, amplified and refined biofield information to the subject, wherein the second signal is provided to the input plate based on the user action received through the start button, and the second signal enables continuous or non-continuous transmission of the biofield information from the fluid contained in the first vial or the second vial secured to the input plate vial well to the subject placed on the output plate through the galvanic connection, enhancing the biofield information by creating a subsequent change in the subject and the one or more amplification knobs are set to zero reading during the transmission.

12. The biofield apparatus as claimed in claim 11, wherein the biofield information associated with the subject comprises light information.

13. The biofield apparatus as claimed in claim 11, wherein the biofield information stored in the fluid contained in the first vial is transmitted to the subject, with the first vial removably coupled to the input plate vial well and the subject galvanically coupled to the output plate, and wherein the biofield information from the fluid contained in the first vial is transmitted to the subject based upon receipt of a second signal at the input plate.

* * * * *